United States Patent
Remers et al.

(10) Patent No.: US 6,476,236 B1
(45) Date of Patent: Nov. 5, 2002

(54) SYNTHESIS OF 2-CYANOAZIRIDINE-1-CARBOXAMIDE

(75) Inventors: William Remers, Tuscon, AZ (US); Bashyam Iyengar, Tuscon, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 0 days.

(21) Appl. No.: 09/995,265

(22) Filed: Nov. 26, 2001

(51) Int. Cl.[7] .............................................. C07D 203/12

(52) U.S. Cl. ...................................................... 548/966

(58) Field of Search ......................................... 548/966

(56) References Cited

U.S. PATENT DOCUMENTS

| 4,083,987 A | 4/1978 | Bicker et al. |
| 4,376,731 A | 3/1983 | Bosies et al. |

OTHER PUBLICATIONS

Iyengar BS, Dorr RT, Alberts DS, et al. Novel antitumor 2–cyanoaziridine–1–carboxamides. J Med Chem 1999;42:510–4.*

* cited by examiner

*Primary Examiner*—Joseph K. McKane
*Assistant Examiner*—Jennifer C. Murphy
(74) *Attorney, Agent, or Firm*—Townsend and Townsend and Crew LLP

(57) ABSTRACT

The present invention provides a process for producing an aziridine-1-carboxamide of the formula:

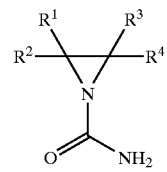

I from an aziridine of the formula:

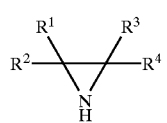

II and an isocyanate of the formula $R^5-N=C=O$, where $R^1$, $R^2$, $R^3$, $R^4$ and $R^5$ are those defined herein. In addition, the present invention also provides a process for producing a 4-imino-1,3-diazabicyclo[3.1.0]-hexan-2-one of the formula:

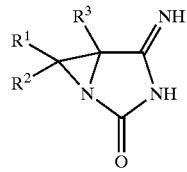

from the aziridine-1-carboxamide of Formula I.

5 Claims, No Drawings

SYNTHESIS OF 2-CYANOAZIRIDINE-1-CARBOXAMIDE

STATEMENT AS TO RIGHTS TO INVENTIONS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of Grant No. SR01 GM 52795-06 awarded by National Institute of Health.

FIELD OF THE INVENTION

The present invention relates to a process for producing an aziridine-1-carboxamide compound, and a process for producing a 4-imino-1,3-diazabicyclo[3.1.0]-hexan-2-one compound from the aziridine-1-carboxamide compound.

BACKGROUND OF THE INVENTION

Aziridine-1-carboxamide compounds and derivatives thereof have a variety of therapeutical useful activities such as immunostimulant activities. See, for example, U.S. Pat. No. 4,376,731. In addition, aziridine-l-carboxamide compounds are useful intermediates for a wide variety of pharmaceutically active compounds including 4-imino-1,3-diazabicyclo[3.1.0]-hexan-2-one and its derivatives. See, for example, U.S. Pat. No. 4,083,987. As these references show, 2-cyanoaziridine-1-carboxamide or its derivatives are particularly useful both as a pharmaceutical agents and as intermediates for other pharmaceutically useful compounds.

However, some of the conventional methods for producing 2-cyanoaziridine-1-carboxamide involve generation of a toxic reagent and/or potentially explosive reaction conditions. For example, a synthetic method for producing 2-cyanoaziridine-1-carboxamide as disclosed by Uwe Bicker in East German Patent 110,492 involves passing a hot toxic isocyanic acid into ether which is generated from pyrolysis of cyanuric acid. This is a dangerous procedure because high flammability of ether and generation of a highly toxic blistering agent isocyanic acid. Moreover, due to the dangerous conditions, a special apparatus is generally required for this process.

Therefore, there is a need for a safer alternative method for producing aziridine-1-carboxamide compounds.

SUMMARY OF THE INVENTION

One aspect of the present invention provides a process for producing an aziridine-1-carboxamide of the formula:

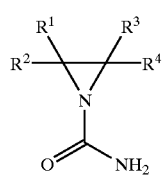

said process comprising:
(a) contacting an aziridine of the formula:

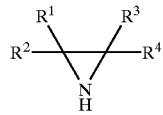

with an isocyanate of the formula $R^5$—N=C=O under conditions sufficient to produce an N-acylated aziridine of the formula:

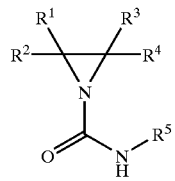

wherein
each of $R^1$, $R^2$ and $R^3$ is independently hydrogen or $C_1$–$C_6$ alkyl;
$R^4$ is cyano, carboxamide or carboxylic acid ester; and
$R^5$ is a moiety of the formula —C(=O)—$R^6$, where $R^6$ is haloalkyl, and (b) removing the $R^5$ group by contacting the N-acylated aziridine with a nucleophilic reagent under conditions sufficient to produce the aziridine-1-carboxamide of Formula I.

Another aspect of the present invention provides a process for producing a 4-imino-1,3-diazabicyclo[3.1.0]-hexan-2-one of the formula:

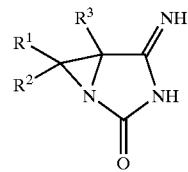

from the aziridine-1-carboxamide of Formula I, where $R^1$, $R^2$ and $R^3$ are those defined above.

DEFINITIONS

"Alkyl" refers to a linear fully-saturated hydrocarbon moiety having one to ten, preferably one to six, carbon atoms or a branched fully saturated hydrocarbon moiety having three to ten, preferably three to six, carbon atoms.

"Carboxamide" refers to a moiety of the formula —C(=O)$NR^aR^b$, where each of $R^a$ and $R^b$ is independently hydrogen, alkyl, cycloalkyl, aryl or aralkyl.

"Carboxylic acid ester" refers to a moiety of the formula —C(=O)$OR^a$, where $R^a$ is alkyl, cycloalkyl, aryl or aralkyl.

"Haloalkyl" refers to an alkyl moiety, as defined above, in which one or more hydrogen atoms attached to the carbon backbone have been replaced with one or more halides, preferably chloride, bromide or fluoride. Exemplary haloalkyl groups include mono-, di- and trichloromethyl, mono-, di- and trifluoromethyl and the like.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

DETAILED DESCRIPTION OF THE INVENTION

One aspect of the present invention provides a process for producing an aziridine-1-carboxamide of the formula:

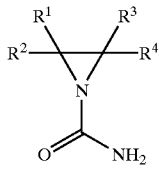
I where $R^1$, $R^2$, $R^3$ and $R^4$ are those defined above. The processes of the present invention comprise contacting an aziridine of the formula:

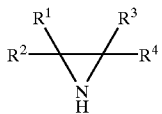
II with an isocyanate of the formula $R^5$—N=C=O under conditions sufficient to produce an N-acylated aziridine of the formula:

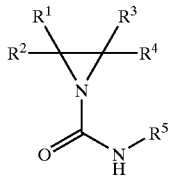
III where $R^1$, $R^2$, $R^3$, $R^4$ and $R^5$ are those defined herein.

The processes of the present invention also comprise removing the $R^5$ group by contacting the N-acylated aziridine of Formula III with a nucleophilic reagent under conditions sufficient to produce the aziridine-1-carboxamide of Formula I.

Preferably, $R^5$ is haloacetyl. More preferably $R^5$ is trichloroacetyl, dichloroacetyl, chloroacetyl, trifluoroacetyl or tribromoacetyl. More preferably, $R^5$ is trichloroacetyl.

Preferably, $R^4$ is cyano.

In one particular embodiment, $R^1$, $R^2$ and $R^3$ are hydrogen.

The reaction between the aziridine-1-carboxamide of Formula II and the isocyanate can be conducted at a wide range of reaction temperature in an inert solvent, i.e., a solvent that is non-reactive to the starting materials. Conveniently, however, the reaction is conducted at room temperature or less. Typically, the reaction temperature range is from about −10° C. to about 5° C. Suitable reaction solvents include inert aprotic solvents such as aromatic solvents, e.g., toluene, xylenes, benzene, and the like; ethers, e.g., diethyl ether, tetrahydrofuran, and the like; and halogenated solvents, e.g., dichloromethane, chloroform, and the like.

The resulting N-acylated aziridine of Formula III can be purified prior to removing the $R^5$ group. Often, however, the N-acylated aziridine of Formula III can be used directly on the next step without further purification.

The $R^5$ group can be removed from the N-acylated aziridine of Formula III by reacting with a nucleophilic reagent to produce the aziridine-1-carboxamide of Formula I. The reaction is conveniently carried out in an anhydrous alcoholic solvent, such as methanol, ethanol, isopropanol and propanol. Suitable nucleophilic reagents include ammonia and amines. Typically, a mixture of ammonia in methanol is used to remove the $R^5$ group from the N-acylated aziridine of Formula III. Often, the reaction is conveniently conducted at about 0° C.

The processes of the present invention provide the aziridine-1-carboxamide of Formula I from the aziridine of Formula II in an overall yield of at least about 70%. Preferably, in an overall yield of at least about 75%, and more preferably at least about 80%.

One of the advantages of processes of the present invention includes eliminating a need for potentially flammable conditions because no pyrolysis of any starting material is needed. In addition, processes of the present invention avoid generating toxic isocyanic acid. Furthermore, starting materials for the present invention are commercially available or can be readily prepared without requiring any special apparatus.

When at least one of $R^1$, $R^2$, $R^3$ and $R^4$ is cyano, the aziridine-1-carboxamide of Formula I can be converted to a 4-imino-1,3-diazabicyclo[3.1.0]-hexan-2-one. For example, 2-cyanoaziridine-1-carboxamide of the formula:

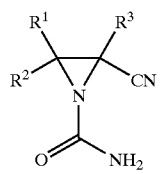
IV can be prepared using the processes described above. This 2-cyanoaziridine-1-carboxamide of Formula IV can be converted to a 4-imino-1,3-diazabicyclo[3.1.0]-hexan-2-one of the formula:

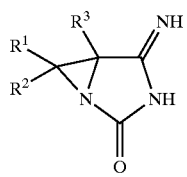
V by reacting with a base.

The 4-imino-1,3-diazabicyclo[3.1.0]-hexan-2-one of Formula V can exist in one or more tautomeric form as shown below:

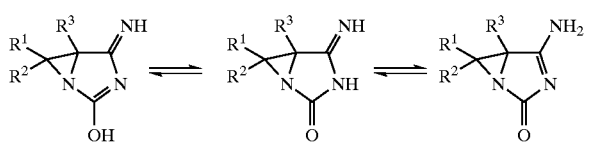

Thus, the term "4-imino-1,3-diazabicyclo[3.1.0]-hexan-2-one of Formula V" includes all of the tautomers shown above.

Typically, the above described cyclization is conducted in a substantially anhydrous, polar, organic solvent, preferably in an alcohol solvent such as methanol, ethanol, isopropanol and propanol. In some cases, and in particular where $R^1$, $R^2$ and $R^3$ are hydrogen, the resulting 4-imino-1,3-diazabicyclo[3.1.0]-hexan-2-one of Formula V crystallizes readily from the reaction solvent, thereby making the isolation of the product simple and facile.

While any base having a sufficient pKa to promote the cyclization can be used, the present inventors have found that surfactants comprising alcohol and ethoxylates, alkoxylates, in particular triton B® (Union Carbide), are particularly useful in producing the 4-imino-1,3-diazabicyclo[3.1.0]-hexan-2-one of Formula V from the 2-cyanoaziridine-1-carboxamide of Formula IV.

Additional objects, advantages, and novel features of this invention will become apparent to those skilled in the art upon examination of the following examples thereof, which are not intended to be limiting.

EXAMPLES

Example 1

This example illustrates synthesis of 2-cyanoaziridine-1-[N-(trichloroacetyl)]-carboxamide.

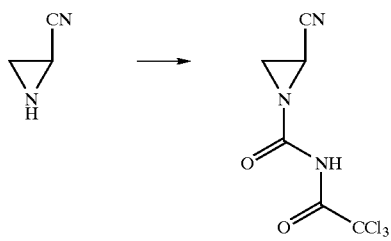

A 1-L, three-neck flask fitted with a mechanical stirrer, thermocouple, and a nitrogen inlet was charged with 200 mL of toluene and 80 g of trichloroacetylisocyanate. The mixture was cooled to −10° C. with dry-ice/ethanol bath and a suspension of 28.6 g of 2-cyanoaziridine (Aldrich Chemical Co., Milwaukee, Wis.) in toluene was added over 1 hr in portions while maintaining the temperature of the mixture between −10° C. and 5 ° C. After the addition was complete, the reaction mixture was stirred at 0° C. for 1 hr. It was then stored in a refrigerator overnight at 5° C. The solid that separated was collected by filtration and washed with toluene. It was then triturated with 300 mL of methyl tert-butyl ether for 1 hr. The mixture was filtered and the solid was dried under vacuum to provide 90 g (83% yield) of 2-cyanoaziridine-1-[N-(trichloroacetyl)]-carboxamide. NMR (CDCl$_3$) δ: 1.6 (bs, 1H), 2.87 (d, 1H), 2.97 (d, 1H), 3.35 (q, 1H) and 8.75 (bs, 1H).

Example 2

This example illustrates synthesis of 2-cyanoaziridine-1-carboxamide.

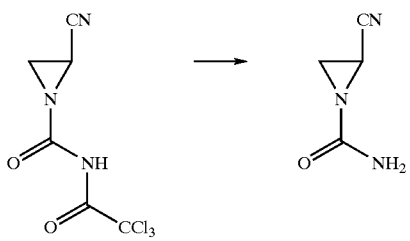

A 1-L, round bottom flask fitted with a magnetic stirrer and a nitrogen inlet was charged with 350 mL of methanol and 154 mL of 7N ammonia in methanol. The mixture was cooled to 0° C. and 102 g of 2-cyanoaziridine-1-[N-(trichloroacetyl)]-carboxamide (see Example 1) was added in portions over 5–10 min. The reaction mixture was stirred at 0° C. for 1.5 hr. The reaction mixture was then concentrated by removing ammonia and methanol in vacuum. The resulting residue solid was treated with toluene to dissolve the trichloroacetamide by-product. The solid residue contained 45.8 g of the title compound, which was used without further purification in the next step (see Example 3). NMR (CDCl$_3$) δ: 1.7 (bs, 1H), 2.55 (d, 1H), 2.58 (d, 1H), 3.06 (dd, 1H) and 8.75 (bd, 2H).

Example 3

This example illustrates synthesis of 4-imino-1,3-diazabicyclo[3.1.0]-hexan-2-one, i.e., Imexon.

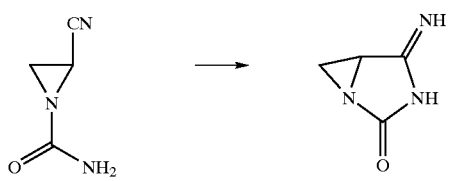

A 1-L, round bottom flask fitted with a magnetic stirrer and a nitrogen inlet was charged with 400 mL of methanol and 45.8 g of 2-cyanoaziridine-1-carboxamide (See Example 2). To this mixture was added a solution of 40% of triton B® in 10 mL of methanol. The resulting mixture was stirred at room temperature overnight and then cooled to 0° C. The solid product was then filtered, washed successively with ethanol and methanol, and dried under vacuum to provide 27 g (61% yield from 2-cyanoaziridine-1-[N-(trichloroacetyl)]-carboxamide) of the title compound, which had a NMR spectrum identical with that of an authentic sample of Imexon.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A process for producing an aziridine-1-carboxamide of the formula:

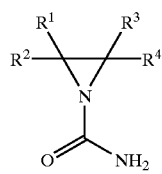

I said process comprising:

(a) contacting an aziridine of the formula:

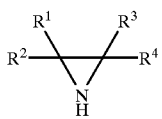

II with an isocyanate of the formula $R^5$—N=C=O under conditions sufficient to produce an N-acylated aziridine of the formula:

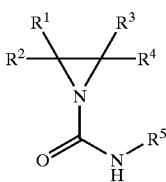

III wherein
each of $R^1$, $R^2$ and $R^3$ is independently hydrogen or $C_1$–$C_6$ alkyl;
$R^4$ is cyano, carboxamide or carboxylic acid ester; and
$R^5$ is a moiety of the formula —C(=O)—$R^6$, where $R^6$ is haloalkyl, and
(b) removing the $R^5$ group by contacting the N-acylated aziridine with a nucleophilic reagent under conditions sufficient to produce the aziridine-1-carboxamide of Formula I.

2. The process of claim 1, wherein $R^5$ is selected from the group consisting of trichloroacetyl, dichloroacetyl, chloroacetyl, tribromoacetyl and trifluoroacetyl.

3. The process of claim 2, wherein $R^5$ is trichloroacetyl.

4. The process of claim 3, wherein the nucleophilic reagent comprises ammonia.

5. The process of claim 1, wherein $R^1$, $R^2$ and $R^3$ are hydrogen and $R^4$ is cyano.

* * * * *

UNITED STATES PATENT AND TRADEMARK OFFICE
CERTIFICATE OF CORRECTION

PATENT NO. : 6,476,236 B1
DATED : November 5, 2002
INVENTOR(S) : William A. Remers et al.

It is certified that error appears in the above-identified patent and that said Letters Patent is hereby corrected as shown below:

Title page,
Item [75], Inventors, "Bashyam Iyengar" should read -- Bhashyam Iyengar --.

Signed and Sealed this

Twenty-first Day of December, 2004

JON W. DUDAS
*Director of the United States Patent and Trademark Office*